United States Patent [19]

Haley et al.

[11] Patent Number: 4,672,111

[45] Date of Patent: Jun. 9, 1987

[54] 5-AZIDO-DEOXYURIDINE COMPOUNDS AND METHOD OF SYNTHESIS OF THE SAME

[75] Inventors: Boyd E. Haley; Robert K. Evans, both of Laramie, Wyo.

[73] Assignee: University of Wyoming, Laramie, Wyo.

[21] Appl. No.: 726,145

[22] Filed: Apr. 23, 1985

[51] Int. Cl.[4] .................. C07H 19/10; C07H 19/067; C07H 19/073

[52] U.S. Cl. .......................................... 536/29; 536/23

[58] Field of Search ...................... 536/23, 29

[56] References Cited

U.S. PATENT DOCUMENTS 3,235,363  2/1966  Luckenbaugh et al. ............... 71/2.5
3,792,040  2/1974  Moffatt ................................. 536/23
3,852,433  12/1974 Tamura ................................. 536/29

OTHER PUBLICATIONS

Chemical Abstracts 94:98536t (1981).
Bradshaw, T., Chem. Soc. Rev. vol. 6, 1971, pp. 52–57, "5-Substituted Pyrimidine Nucleosides and Nucleotides...".
Balzarini, J., Biochem. Pharma. vol. 31, N022, 3673–3682, Pergamon Press 1982, "5-Substituted-2-Deoxyuridines...".
Huang et al., J. Org. Chem. vol. 42, No. 24, 3821–3824 (1977) "Nitration of Pyrimidine Bases and Nucleotides...".
Luhrmann et al. "Covalent Binding of Uridine-Oligonucleotides..." Febs. Letters, vol. 32, No. 1, 55–58 (1973).
Roberts et al., "Uridine and Cytidine Derivatives" J. Am. Chem. Soc. 74, 668–669 (1975).
Michelson, "Synthesis of Nucleotide Anhydrides..." Biochimica Et Biophysica Acta 91, 1–13 (1964).
Bradshaw, et al. "5-Substituted Pyrimidine Nucleosides and Nucleotides..." Chem. Soc. Rev. 6, 43–63 (1971).
Balzarini, et al., "5-Substituted 2'-Deoxyuridines..." Biochemical Pharmacology, 31, 3673–3682 (1982).
Scheit, "Nucleotide Analogs..." Wiley-Interscience Publications (1980) pp. 237–253.
Guillory, et al., "Photoaffinity Labeling..." Federation Proceedings, 42, 2826–2830 (Aug. 1983).

Primary Examiner—Johnnie R. Brown
Attorney, Agent, or Firm—Ralph F. Crandell

[57] ABSTRACT 5-azido-2-'-deoxyuridine nucleoside and nucleotide compounds and a method of producing them. The method involves reacting a 5'-deoxyuridine compound with nitrosonium tetrafluoroborate to produce a 5-nitro-deoxyuridine compound. The 5-nitro-deoxyuridine compound is reduced to a 5-amino-deoxyuridine compound in the presence of metallic zinc. The 5-amino-deoxyuridine compound is acidified and reacted with sodium nitrite to produce a 5-diazo-deoxyuridine compound. The diazo-deoxyuridine compound is then reacted with sodium azide to produce a 5-azido-deoxyuridine compound. The latter, in the monophosphate form, is further reacted with diphenylchlorophosphate to produce the photoactive triphosphate, 5-azido-2'-deoxyuridine-5'-triphosphate or 5-azido-dUTP. The photoactive compound, when added to DNA in an in vitro synthesis reaction, produces photoactive DNA.

7 Claims, 5 Drawing Figures

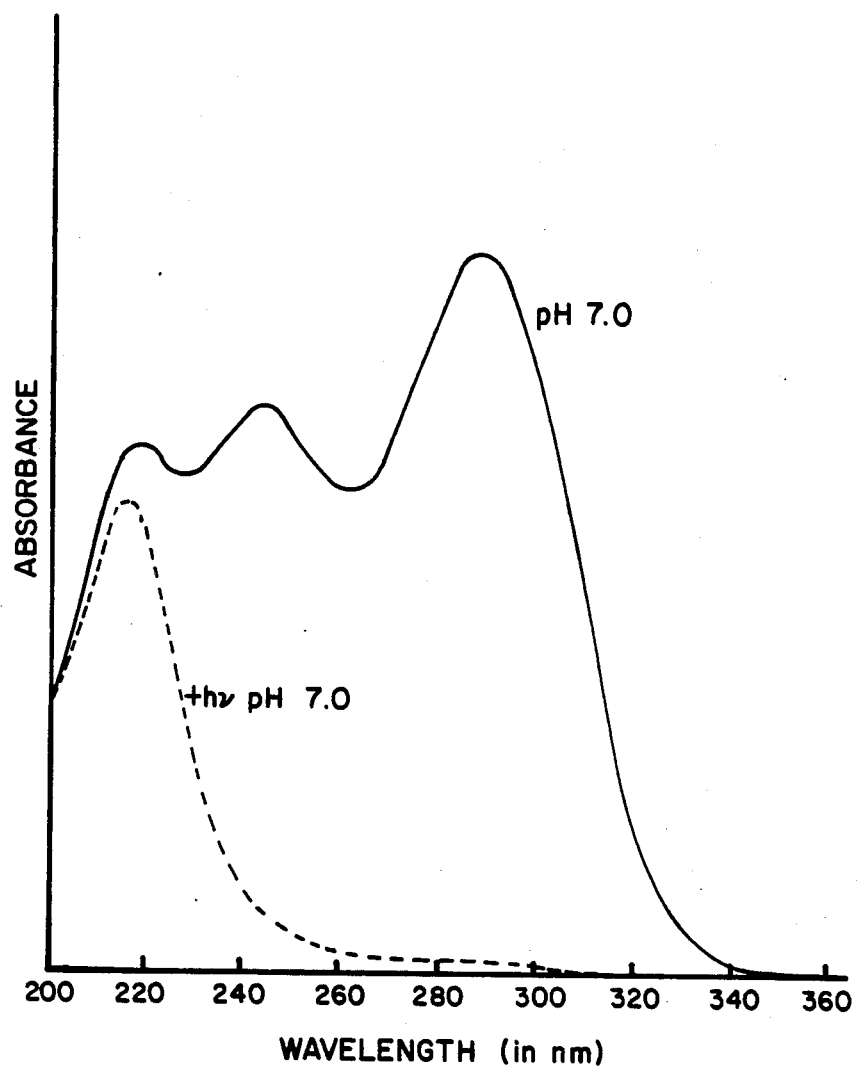
Fig_1

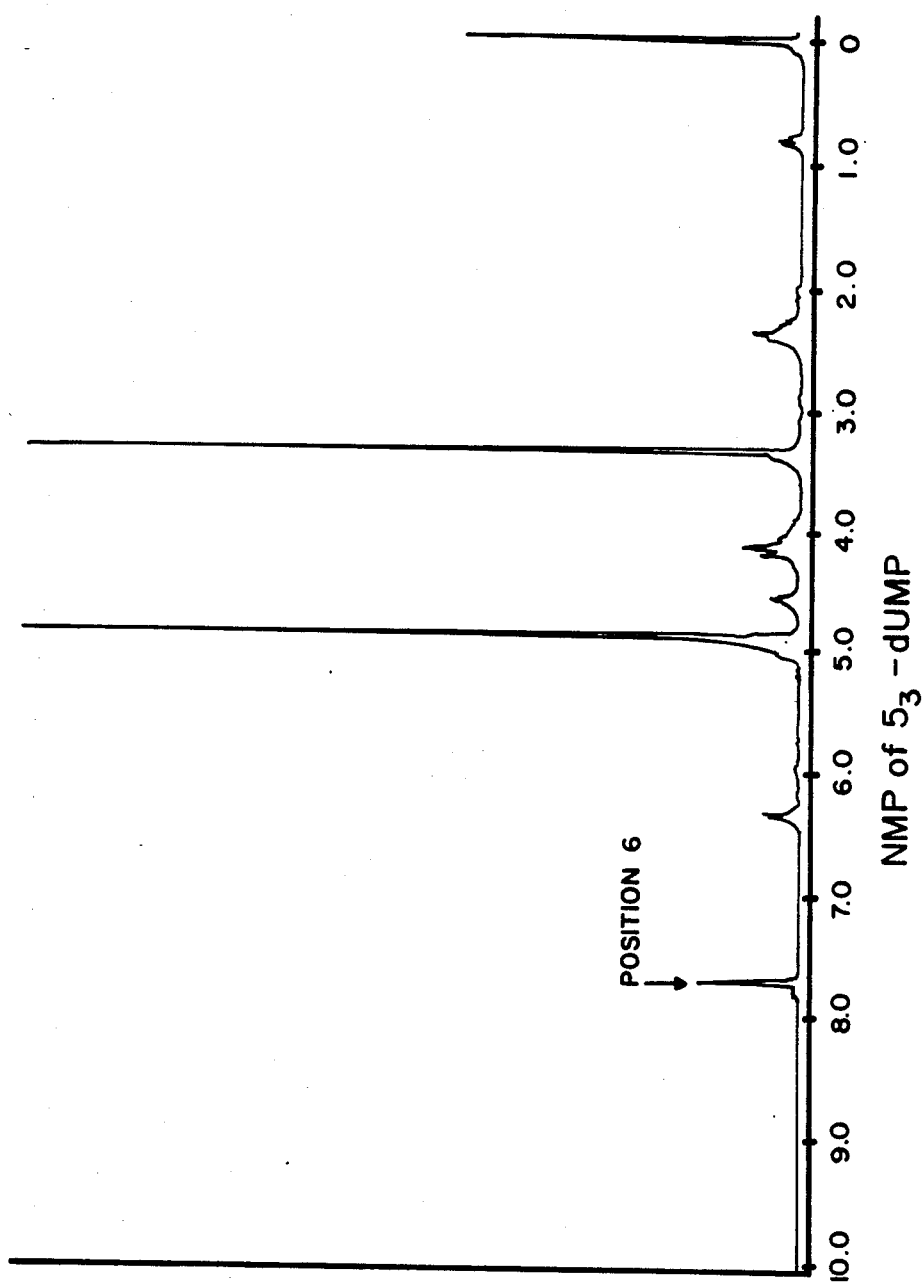
Fig._2A  NMP of 5₃-dUMP

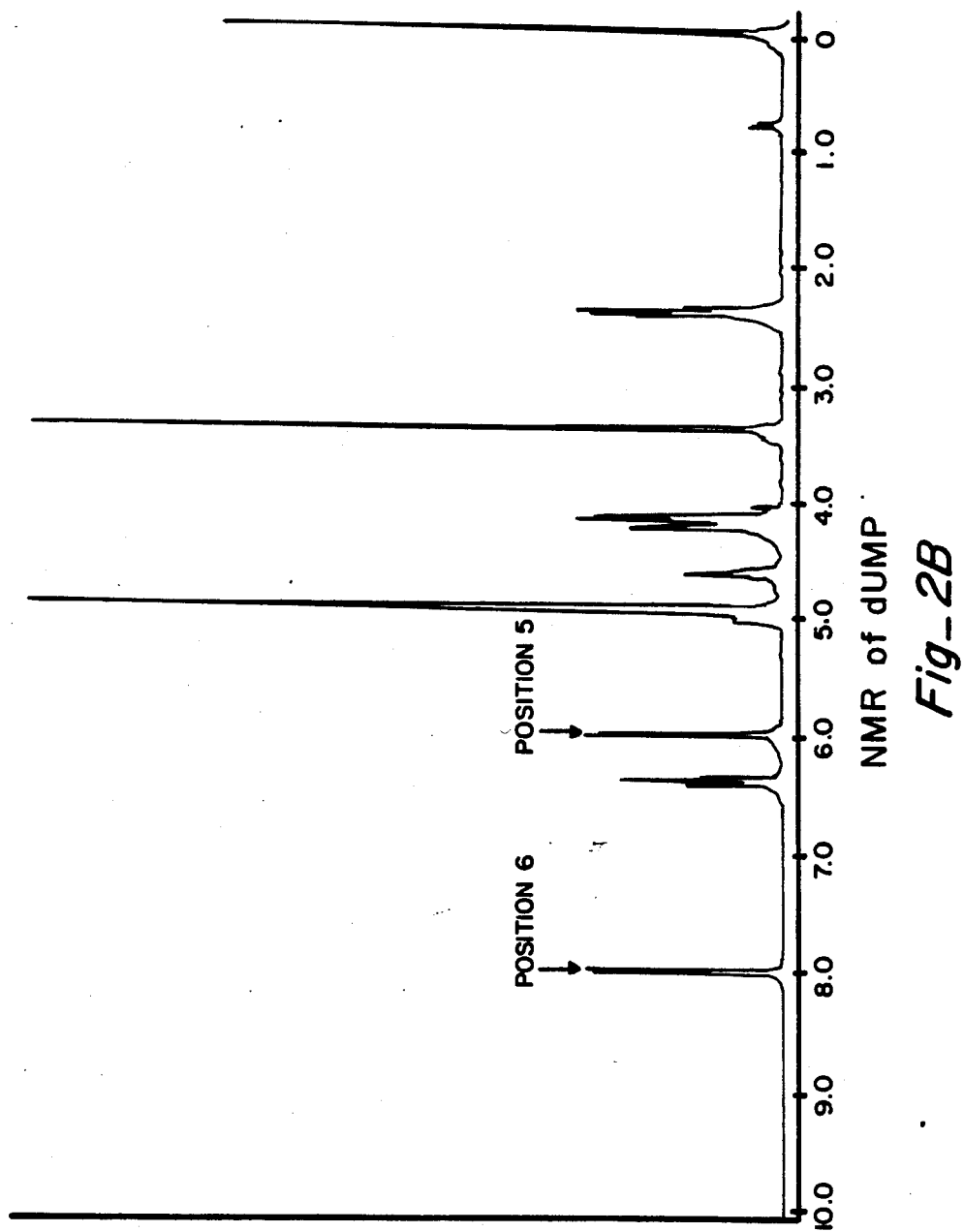

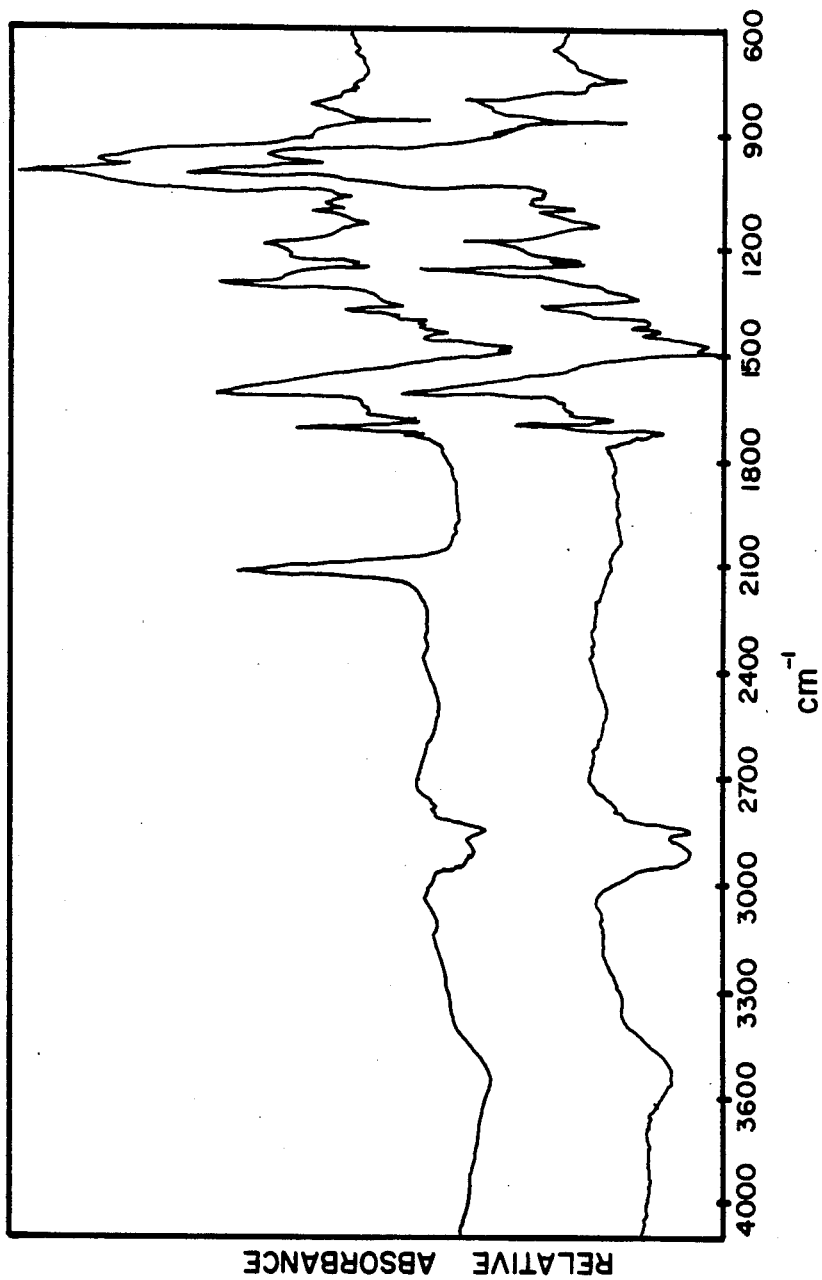
Fig_3

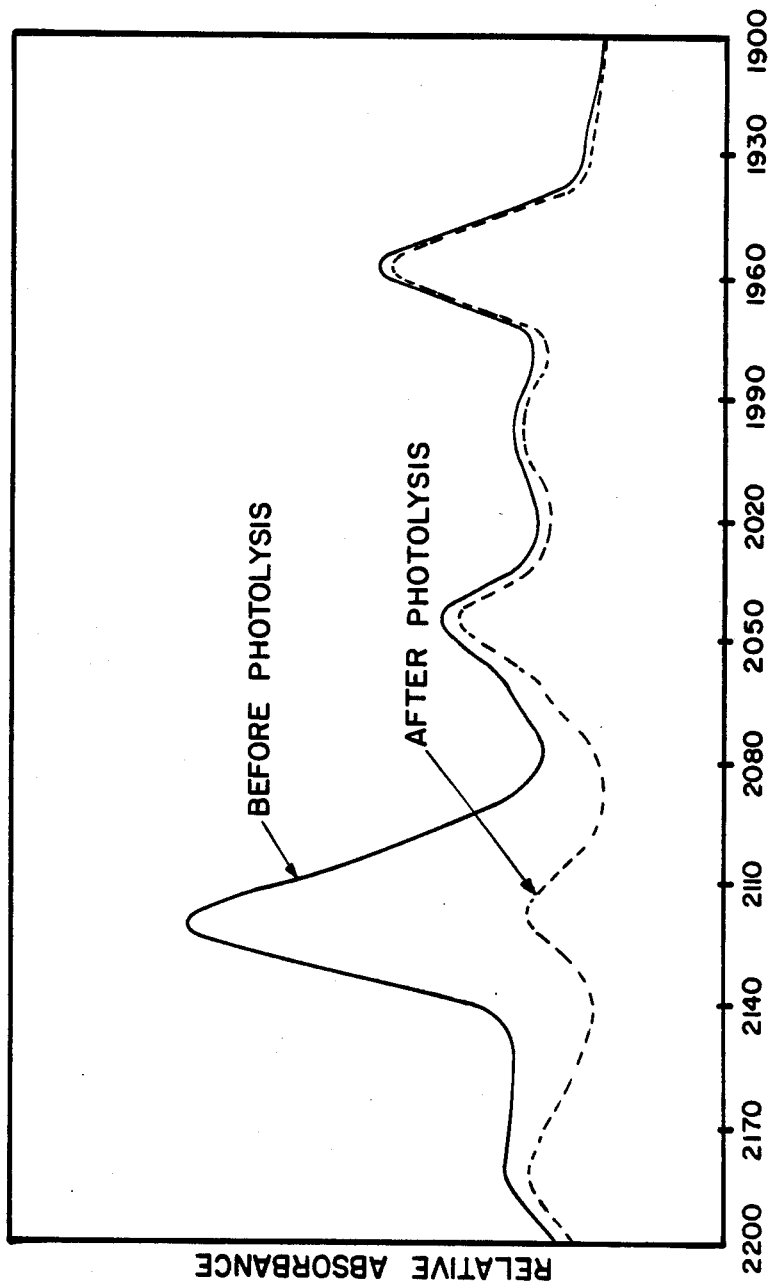
Fig_4

5-AZIDO-DEOXYURIDINE COMPOUNDS AND METHOD OF SYNTHESIS OF THE SAME

BACKGROUND OF THE INVENTION

Field of the Invention

The present invention relates to 5-azido-uracil containing nucleoside and nucleotide compounds and methods for producing the same.

OBJECTS AND SUMMARY OF THE INVENTION

The principal object of the present invention is to produce novel photoactive nucleotides and nucleosides. A related object is to produce novel photoactive nucleotides and nucleosides which allow the photoaffinity labeling of materials such as the synthesis of photoactive DNA. A further object of the present invention is to provide a novel method for the production of photoactive nucleosides and nucleotides having the foregoing characteristics.

In accordance with the foregoing objects, the present invention resides in novel nucleosides containing the photoactive base 5-azido uracil, and more particularly to the nucleotides 5-azido-2'-deoxyuridine-5'-triphosphate and 5-azido-2'-deoxyuridine-5'-monophosphate. A novel method for producing the foregoing nucleosides and nucleotides involves a five step synthesis beginning with 5'-dUMP from which 5-nitro-dUMP is produced as the first step in the synthesis. The nitro compound which is then reduced to 5-amino-dUMP. The 5-amino-dUMP is then diazotized with nitrous acid, and the diazo salt is immediately reacted with sodium azide to produce 5-$N_3$-dUMP in high yield. Additional phosphate radicals are coupled to diphenylchlorophosphate-activated 5-$N_3$-dUMP to yield 5-$N_3$-dUTP.

DESCRIPTION OF THE DRAWINGS

FIG. 1 is a diagrammatic representation of the ultra violet spectrum (U.V.) of 5-$N_3$-dUMP.

FIG. 2A is a diagramatic representation of the nuclear magnetic response (NMR) spectrum of the H+ form of 5-$N_3$-dUMP in $D_2O$.

FIG. 2B is a diagrammatic representation of the nuclear magnetic response (NMR) spectrum of 5'-dUMP.

FIG. 3 is a diagramatic representation of the infrared (IR) spectrum of 5-$N_3$-dUMP and of dUMP.

FIG. 4 is a diagramatic representation showing the effect of UV light on the infrared absorption peak at 2117 $cm^{-1}$.

DESCRIPTION OF THE PREFERRED EMBODIMENT

Nucleotides and nucleosides containing the photoactive base, 5-azido-uracil, can be synthesized by the present method. The various 5-$N_3$-Uracil nucleotide and nucleoside compounds that can be made are shown by the following general formula:

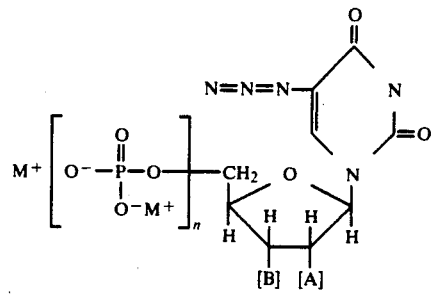

wherein:

$M^+$ = any monovalent or divalent cation;

$n = 1-5$;

$A = H$ or $OH$;

$B = [-PO_4]_{1-3}$, H, or OH.

The synthesis of the photoactive nucleotide 5-azido-2'-deoxyuridine-5'-triphosphate (5-$N_3$-dUTP) is a five step process beginning with 5'-deoxyuridine-monophosphate (5'-dUMP). The sequence of the five step synthesis is illustrated schematically as follows:

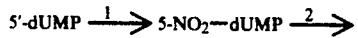

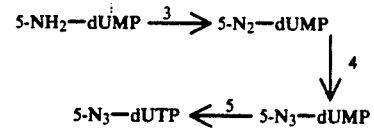

The synthesis begins with the compound 5'-deoxyuridine-monophosphate (sometimes referred to as 5'-dUMP). This compound is a known nucleotide which is readily available or synthesizable. The 5'-dUMP is initially changed to the H+ form by ion exchange, purified and dried. The dried 5'-dUMP is placed in an anhydrous dimethylformamide (DMF) solution to which nitrosonium tetrafluoroborate is added to nitrate the 5'-dUMP to 5-nitro-dUMP (5-$NO_2$-dUMP).

An acidified solution of 5-$NO_2$-dUMP is reduced in the presence of metallic zinc to 5-amino-dUMP (5-$NH_2$-dUMP). The amino product is then purified. The purified amino compound is then used to produce the azido product in two steps. To this end, the amino product is acidified, following which sodium nitrite ($NaNO_2$) is added to produce the diazo salt 5-$N_2^+$-dUMP which is not isolated. The reaction mixture containing 5-$N_2^+$-dUMP is then treated with sodium azide ($NaN_3$) to produce the azido compound (5-$N_3$-dUMP) in high yield. The reaction mixture is passed through a G-10 sephadex column. The 5-$N_3$-dUMP product is eluted and concentrated under vacuum.

Pyrophosphate is coupled to the 5-$N_3$-dUMP by a known, published method with certain modifications. Specifically, the TEA salt of 5-$N_3$-dUMP is activated with diphenylchloroposphate in DMF. After activation, the reaction mixture is added to an excess of the tetrabutylammonium salt of pyrophosphate. After the reaction has proceeded for the proper time, 5-$N_3$-dUTP is separated and recovered.

The following is a detailed description of the five step process:

Step 1—Synthesis of 5-$NO_2$-dUMP from 5'-dUMP

The disodium salt of 5'-dUMP (200 mg, 236 umoles) was dissolved in 3 ml $H_2O$ and applied to a column of Dowex 50 w ($H^+$ form, 10 cm×3 cm) resin. The $H^+$ form of 5-dUMP was eluted from the column with distilled water. The $H^+$ form of 5'-dUMP was then placed in a round bottom flask and evaporated to dryness under reduced pressure at 50° C. The dried material was resuspended and co-evaporated in methanol (0.01% $H_2O$) three times to remove water. Anhydrous dimethylformamide (DMF) (5.0 ml) was added to the dry 5'-dUMP and the resulting solution stirred at 25° C. until clear. Nitrosonium tetrafluoroborate (176 mg, 2360 umoles) was added while stirring the 5'-dUMP reaction mixture. The nitration reaction was allowed to proceed for 5 minutes, after which the reaction was stopped by the addition of 0.5 ml of $H_2O$. The reaction mixture was then evaporated to near dryness at 40° C., after which 5.0 ml of 1N HCl was added. This acidified solution was evaporated to near dryness under reduced pressure at 30° C. The product was then co-evaporated several times using 5.0 ml of $H_2O$ each time. After the last co-evaporation in $H_2O$, the product was diluted with $H_2O$ to a final volume of approximately 3 ml. Concentrated $NH_4OH$ was added to raise the pH to 7.0±1.0. This neutralized sample was applied to a column of DEAE-cellulose (30 cm×1.5 cm., $HCO_3^-$ form) and eluted with a 400 ml linear gradient of 0 to 0.25M triethylammonium bicarbonate (TEA-$HCO_3$). The 5-$NO_2$-dUMP eluted from the column was identified by its known UV spectrum (Huang, G., and Torrence, P. F. (1977) J. Org. Chem. 42, 3821–3824), and its thin layer chromatographic (TLC) properties on cellulose using solvent system A: isobutyric acid/$NH_4OH$/$H_2O$ (66:1:33, v/v). The 5-$NO_2$-dUMP containing fractions were pooled and the solution evaporated to dryness at 40° C. under reduced pressure. Co-evaporation with methanol was performed until TEA-$HCO_3$ was not present. The final product was stored in distilled $H_2O$ at 10° C. until used for synthesis of 5-$NH_2$-dUMP. Yield was 98%, based on the UV spectrum of the reaction mixture before column chromatography.

Step 2—Synthesis of 5-$NH_2$-dUMP from 5-$NO_2$-dUMP

Zinc metal filings (15 g) were placed in conentrated HCl for 10 minutes. The filings were then washed with distilled water. A solution of 5-$NO_2$-dUMP (5.0 ml, 100 umoles) in water was acidified by adding 250 ul of 1N HCl. This acidified solution containing 5-$NO_2$-dUMP was then poured over the cleaned metal filings and stirred for 5 minutes at 25° C. Then another 250 ul of 1N HCl were added and allowed to react for 5 minutes. The acidified solution was separated from the Zn metal filings by filtration and dried down to a volume of 1 to 3 ml by evaporation under reduced pressure at 40° C. The 5-$NH_2$-dUMP containing solution was then neutralized with $NH_4OH$ to a pH of 7.0±1.0. The neutralized sample was then applied to a DEAE-cellulose column and eluted as described in step 1. The 5-$NH_2$-dUMP product was identified by its known UV spectrum (Luhrmann, R., Schwarz, U., and Gassen, H. G., (1973) FEBS letters 32,55–58; Roberts, M., and Visser, D. W. (1975) J. Am. Chem. Soc. 74,668–669). The 5-$NH_2$-dUMP containing fractions were pooled and evaporated to dryness at 40° C. Co-evaporation with methanol was used to remove TEA-$HCO_3$. The final purified product was stored in distilled $H_2O$ at 10° C. until it was used to prepare 5-$N_3$-dUMP. A UV spectrum of the final product before column chromatography indicated a yield of 96% from 5-$NO_2$-dUMP.

Steps 3 and 4—Synthesis of 5-diazo-2'-deoxyuridine-5'-monophosphate (5-$N_{+2}$-dUMP) and 5-azido-2'-deoxyuridine-5'-monophosphate (5-$N_3$-dUMP) from 5-$NH_2$-dUMP The 5-$N_{+2}$-dUMP was not isolated, but was used directly after its synthesis to prepare 5-$N_3$-dUMP. The 5-$NH_2$dUMP (47 umoles) in water was placed in a round bottom flask and evaporated to dryness under reduced pressure at 40° C. 5.0 ml of 1N HCl was added to the dried 5-$NH_2$-dUMP and this reaction mixture was placed in an ice water bath for 15 minutes with stirring. 3.0 ml of a $NaNO_2$ solution (18.4 mM, 55.2 uMoles) at 5° C. was added to the stirring reaction mixture and the reaction was allowed to proceed for 2 minutes. After 2 minutes, 1.5 ml of a 4M $NaN_3$ solution at 5° C. was added and this was allowed to stir on ice for 1 minute. After 1 minute the reaction mix was placed in a 25° C. water bath and allowed to stir for 30 minutes in the dark. After 30 minutes, 8N NaOH was added to give a final pH of 7.0±1.0. The neutralized reaction mix was reduced to a volume of 1 to 2 ml by evaporation at reduced pressure at 20° C. and applied to a G-10 sephadex column previously equilibrated in distilled water. The 5-$N_3$-dUMP product was eluted from the G-10 column with distilled water. The first UV absorbing fraction off the G-10 column contained the 5-$N_3$-dUMP product. Yield of 5-$N_3$-dUMP, based on the UV spectrum of photoactive product off the G-10 column was 90% from 5-$NH_2$-dUMP. The photoactive product off the G-10 column was evaporated to a volume of 1 to 2 ml and applied to a BD-cellulose column ($HCO_3^-$ form). The 5-$N_3$-dUMP was eluted from the BD-cellulose column as described in step 1. The 5-$N_3$-dUMP containing fractions were pooled and evaporated to dryness and co-evaporated with methanol several times to remove TEA-$HCO_3$.

The UV spectrum of 5-$N_3$-dUMP is shown in FIG. 1. The calculated molar extinction coefficient (E) of 5-$N_3$-dUMP at pH 7.0 is 6,210 at 288 nm. The effect of UV light on the absorbance spectrum is shown in FIG. 1 by photolyzing for 1 minute with a hand held UV light (254 nm UVS-11 Mineralight, 6000 u watts/$cm_2$).

The nuclear magnetic resonance (NMR) spectrum was performed on the $H^+$ form of 5-$N_3$-dUMP in $D_2O$. Results of NMR show a disappearance of the 5-proton of 5'-dUMP, (FIG. 2). NMR results also show that the 6-proton which gives a doublet peak in 5'-dUMP gives a singlet peak for 5-$N_3$-dUMP. These NMR data show that the 5-position of 5'-dUMP is substituted in 5-$N_3$-dUMP as expected.

The infrared (IR) spectrum was performed on the $H^+$ form of 5-$N_3$-dUMP in dimethylformamide. As can be seen in FIG. 3, there is a characteristic infrared absorption peak at 2117 $cm^{-1}$ which is indicative of the azido group (N=N=N). FIG. 4 shows the effect of UV light on the infrared absorption peak at 2117 $cm^{-1}$. TLC on cellulose using solvent system A gave an $R_f$ value of 0.42 for 5-$N_3$-dUMP, 0.48 for 5-$NO_2$-dUMP and 0.44 for 5-$NH_2$-dUMP. The 5-$N_3$-dUMP product also gave a positive Dische test (Buchanan, J. G., (1951) Nature 168, 1091), which indicates the presence of deoxyribose.

Step 5—Synthesis of 5-N$_3$-dUTP from 5-N$_3$-dUMP

Pyrophosphate was coupled to 5-N$_3$-dUMP by the method of Michelson (Michelson, A. M. (1964) Biochim. Biophys. Acta 91, 1-13), with the following changes. The TEA salt of 5-N$_3$-dUMP was activited with diphenylchlorophosphate in DMF at 25° C. for 1 hour in the dark. After activation of the 5-N$_3$-dUMP, the reaction mix was added dropwise to 1.0 ml of DMF containing a 50 fold excess of the tetrabutylammonium salt of pyrophosphate. The coupling reaction was allowed to proceed for 1 hour at 25° C. in the dark. 5-N$_3$-dUTP was separated from side products on a DEAE-cellulose column (30 cm × 1.5 cm, HCO$_3^-$ form) using a 400 ml linear gradient of 10 mM to 0.5M TEA-HCO$_3$. 5-N$_3$-dUTP was identified by its UV spectrum, its thin layer chromatographic (TLC) properties on cellulose, and its photoactivity.

When 5-N$_3$-dUTP was tested for its ability to be used by DNA polymerase I, it was found that it could be readily substituted for dTTP to produce photoactive DNA. This shows that the final product definitely has three phosphates at the 5' position, as expected. TLC on cellulose using solvent system A gave an R$_f$ value of approximately 0.16 for 5-N$_3$-dUTP. When the 5-N$_3$-dUTP was photolyzed with UV light prior to its addition to an in vitro DNA synthesis reaction, no DNA synthesis occurred, as measured by acid precipitatable counts using [a$^{32}$P]dATP as the label. When the 5-N$_3$-dUMP containing DNA was tested for photoactivity, it was found to photoincorporate, with long wave UV light, into cellulose filter paper much better than control DNA lacking the 5-N$_3$-dUMP.

While a certain illustrative method and compound have been disclosed in detail herein, it should be understood that there is no intention to limit the invention to the specific forms disclosed. On the contrary, the intention is to cover all modifications, alternatives, equivalents and used falling within the spirit and scope of the invention as expressed in the appended claims.

We claim:

1. 5-azido-2'-deoxyuridine-5'-triphosphate.

2. The method of producing 5-azido-2'-deoxyuridine-5'-triphosphate comprising the steps of:
   (a) reacting 5'-deoxyuridine-monophosphate with nitrosonium tetrafluoroborate to produce 5-nitro-2'-deoxyuridine-5'-monophosphate;
   (b) reducing said 5-nitro-2'-deoxyuridine-5'-monophosphate to 5-amino-2'-deoxyuridine-5'-monophosphate in the presence of metallic zinc;
   (c) acidifying said 5-amino-2'-deoxyuridine-5'-monophosphate and reacting the acidified product with sodium nitrite to produce 5-diazo-2'-deoxyuridine-5'-monophosphate;
   (d) reacting said 5-diazo-2'-deoxyuridine-5'-monophosphate with sodium azide to produce 5-azido-2'-deoxyuridine-5'-monophosphate;
   (e) activating said 5-azido-2'-deoxyuridine-5'-monophosphate by reaction with diphenylchlorophosphate; and
   (f) reacting said activated 5-azido-2'-deoxyuridine-5'-monophosphate with an excess of the tetrabutylammonium salt of pyrophosphate to produce 5-azido-2'-deoxyuridine-5'-triphosphate.

3. 5-N$_3$-uracil compounds having the general formula:

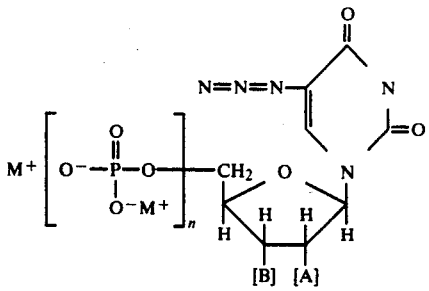

wherein:
M+ = any monovalent or divalent cation;
n = 1-5;
A = H or OH;
B = [−PO$_4$]$_{1-3}$, H, or OH.

4. 5-azido-2'-deoxyurdine-5'-monophosphate.

5. The method of producing 5-azido-2'-deoxyuridine-5'-monophosphate comprising the steps of:
   (a) reacting 5'-deoxyuridine-monophosphate with nitrosonium tetrafluoroborate to produce 5-nitro-2'-deoxyuridine-5'-monophosphate;
   (b) reducing said 5-nitro-2'-deoxyuridine-5'-monophosphate to 5-amino-2'-deoxyuridine-5'-monophosphate in the presence of metallic zinc;
   (c) acidifying said 5-amino-2'-deoxyuridine-5'-monophosphate and reacting the acidified product with sodium nitrite to produce 5-diazo-2'-deoxyuridine-5'-monophosphate; and
   (d) reacting said 5-diazo-2'-deoxyuridine-5'-monophosphate with sodium azide to produce 5-azido-2'-deoxyuridine-5'-monophosphate.

6. 5-diazo-2'-deoxyuridine-5'-monophosphate.

7. The method of producing a 5-azido-2'-deoxyuridine nucleoside compound comprising the steps of:
   (a) reacting a 2'-deoxyuridine compound with nitrosonium tetrafluoroborate to produce a 5-nitro-deoxyuridine compound,
   (b) reducing said 5-nitro-deoxyuridine compound to a 5-amino-deoxyuridine compound in the presence of metallic zinc;
   (c) acidifying said 5-amino-deoxyuridine compound and reacting the acidified product with sodium nitrite to produce a 5-diazo-deoxyuridine compound; and
   (d) reacting said 5-diazo-deoxyuridine compound with sodium azide to produce a 5-azido-deoxyuridine compound.

* * * * *